(12) United States Patent
Kim et al.

(10) Patent No.: US 7,070,910 B2
(45) Date of Patent: Jul. 4, 2006

(54) SILAZANE COMPOUND AMD METHODS FOR USING THE SAME

(75) Inventors: Kyoung-Mi Kim, Anyang-si (KR); Yeu-Young Youn, Seoul (KR); Jae-Ho Kim, Yongin-si (KR); Young-Ho Kim, Yongin-si (KR); Shi-Yong Yi, Sungnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 93 days.

(21) Appl. No.: 11/033,300

(22) Filed: Jan. 12, 2005

(65) Prior Publication Data
US 2005/0164126 A1      Jul. 28, 2005

(30) Foreign Application Priority Data
Jan. 16, 2004     (KR)   .................... 10-2004-0003307

(51) Int. Cl.
*G03C 5/00*     (2006.01)
(52) U.S. Cl. ..................... 430/311; 430/314; 430/315; 430/313; 430/317
(58) Field of Classification Search .............. 430/311, 430/314, 313, 315, 317; 556/412
See application file for complete search history.

(56) References Cited

FOREIGN PATENT DOCUMENTS

| JP | 58-112078 | 7/1983 |
| JP | 7-335603 | 12/1995 |

OTHER PUBLICATIONS

Abstract of JP58188132, Feb. 11, 1983. reference was submitted by applicant but not cited on the 1449.*

* cited by examiner

*Primary Examiner*—Samuel Barts
(74) *Attorney, Agent, or Firm*—Volentine Francos & Whitt, PLLC

(57) ABSTRACT

An adhesive compound for use with a photoresist, the compound represented in accordance with the following chemical formula,

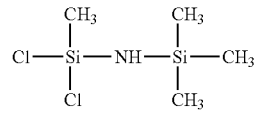

A method for forming a photoresist pattern using the adhesive compound is also disclosed.

13 Claims, 5 Drawing Sheets

US 7,070,910 B2

SILAZANE COMPOUND AMD METHODS FOR USING THE SAME

BACKGROUND OF THE INVENTION

1. Field of the Invention

The present invention generally relates to a novel silazane compound, a method for enhancing adhesive strength of a photoresist film, and a method of forming a photoresist pattern using the silazane compound. More particularly, the present invention generally relates to a (dichlorotetramethyl) disilazane compound, and a method of forming a photoresist pattern using the (dichlorotetramethyl)disilazane compound.

A claim of priority is made to Korean Patent Application No. 2004-3307 filed on Jan. 16, 2004, the content of which is incorporated herein by reference in its entirety.

2. Description of the Related Art

Semiconductor devices with a higher degree of integration and faster response speed are required as information processing systems have rapidly developed. Hence, the technology for manufacturing the semiconductor devices has been developed to improve the degree of integration, reliability, and response speed of the semiconductor devices. Accordingly, a micro-processing technology such as a precisely performed photolithography process is required to improve the degree of integration of the semiconductor device.

In a conventional photolithography process, an organic photoresist film having a pattern layer is formed on a substrate. After exposing the photoresist film to light, the photoresist film is developed to form a photoresist pattern by removing exposed portions of the photoresist film. Afterwards, any remaining photoresist residue is removed from the substrate.

However, since characteristics of the substrate are substantially different from those of the photoresist film, the photoresist film may not be uniformly coated on the substrate. Hence, the photoresist pattern may be lifted from the substrate during the removing process. When a semiconductor device is highly integrated, the above-described problem deteriorates the reliability of the semiconductor device. For example, when a photolithography process is performed to form a bit line having a line width of several tens of nanometers using an argon fluoride (ArF) laser, the photoresist pattern collapses due to the high aspect ratio.

The collapsing of the photoresist pattern can be prevented by enhancing the adhesive strength between a substrate and a photoresist film. A conventional method of increasing the adhesive strength between a resist film and a substrate is disclosed, for example, in Japanese Patent Laid Open Publication No. 1983-188132. In the method, after a substrate is treated with a compound or a solution containing the compound, a resist composition is coated on the substrate to form the resist film. The compound is represented by a chemical formula of $R^1SiX_{3-n}R^2{}_n$ or $[R^1SiR^2{}_2]_2NH$ wherein n is 0, 1 or 2, X is a halogen or —OR' group (R' is an alkyl group having 1 to 3 carbon atoms), $R^1$ is $CH_2$—CH—, $ZOH_2$— (Z is a halogen) or a group including $OCH_2CH$—, and $R^2$ is hydrogen or an alkyl group having 1 to 3 carbon atoms.

Korean Patent Laid Open Publication No. 2001-77196, for example, provides a method of enhancing adhesive strength between a substrate and a photoresist film using a compound in accordance with the chemical structure:

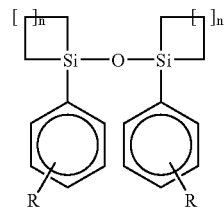

n is an integer of 2 to 8, and R is a hydrogen atom or an alkyl group having 3 to 6 carbon atoms. Here, the hydrogen atom of the alkyl group may be substituted for a halogen atom. However, the compound can only be used for a photoresist film that is exposed using a deep ultra violet (UV) light. Thus, if the compound is used for a photoresist film having strong hydrophobic characteristics that is exposed using an argon fluoride (ArF) laser, which has a relatively short wavelength, the increase of the adhesive strength between the substrate and the photoresist film is minimal. Accordingly, the compound cannot be used for forming a photoresist pattern with a high aspect ratio.

SUMMARY OF THE INVENTION

The present invention provides a novel silazane compound that enhances adhesive strength of a photoresist film exposed using an argon fluoride laser.

The present invention also provides a method of enhancing adhesive strength between a photoresist film and a substrate using the silazane compound.

The present invention still further provides a method of forming a photoresist pattern using the silazane compound.

In accordance with one aspect of the present invention, there is provided a (dichlorotetramethyl)disilazane compound according to the following chemical formula.

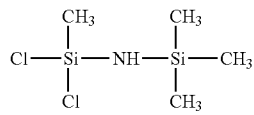

In accordance with another aspect of the present invention, there is provided a method of enhancing adhesive strength of a photoresist film by providing a substrate, forming an adhesive layer on the substrate, the adhesive layer having an adhesive compound in accordance with the following chemical formula,

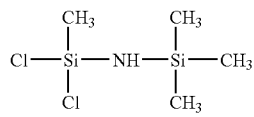

forming a photoresist film on the adhesive layer, and baking the photoresist film formed on the substrate.

In accordance with still another aspect of the present invention, a method for forming a photoresist pattern by providing a substrate, forming an adhesive layer on the substrate containing an adhesive compound having the following chemical formula,

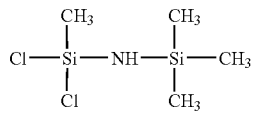

forming a photoresist film on the adhesive layer, baking the photoresist film formed on the substrate, exposing the photoresist film to a light, and developing the photoresist film to form a photoresist pattern on the substrate.

BRIEF DESCRIPTION OF THE DRAWINGS

The above aspects of the present invention will become readily apparent by reference to the following detailed description when considered in conjunction with the accompanying drawings.

DESCRIPTION OF THE INVENTION

Figure 1:
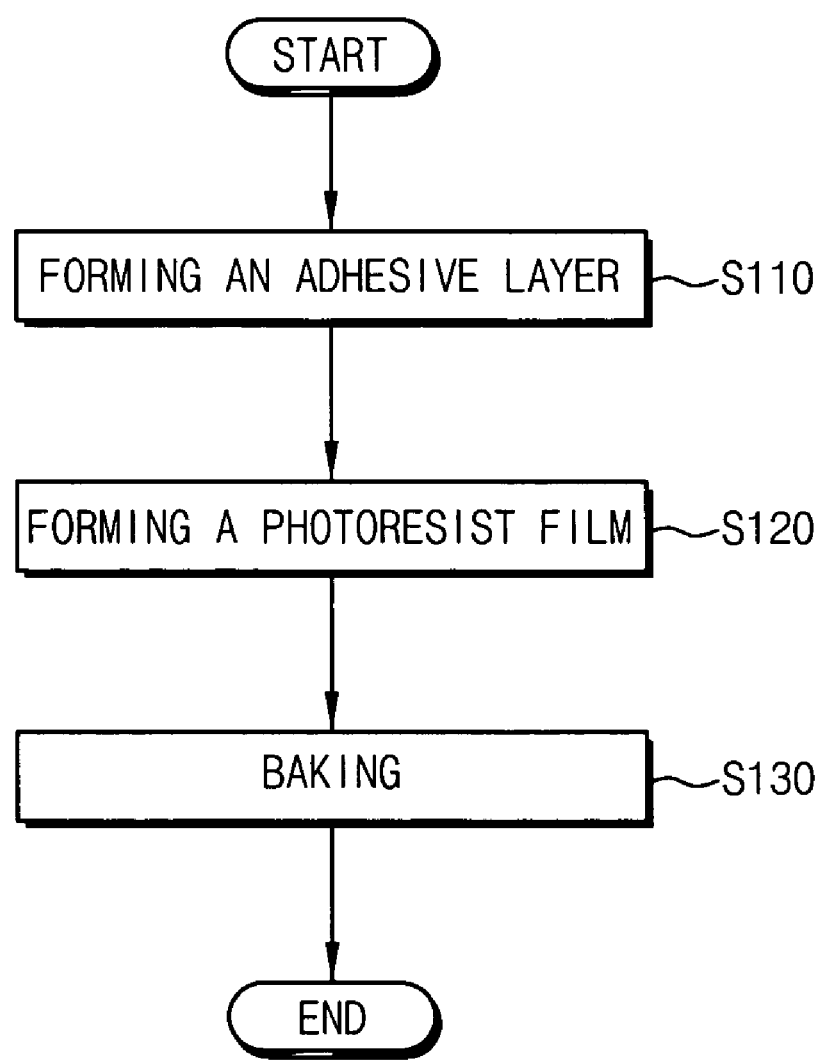
FIG. 1 is a flow chart illustrating a method of enhancing adhesive strength between a photoresist film and a substrate, or between a photoresist film and its underlying structures in accordance with one embodiment of the present invention.

The present invention now will be described more fully hereinafter with reference to the accompanying drawings, in which embodiments of the invention are shown. The present invention may, however, be embodied in many different forms and should not be construed as limited to the embodiments set forth herein; rather, these embodiments are provided as working examples. In the drawings, the thickness of layers and regions are exaggerated for clarity. Like reference numerals refer to similar or identical elements throughout. It will be understood that when an element such as a layer, a region or a substrate is referred to as being "on" or "onto" another element, it can be directly on the other element or intervening elements may also be present.

The present invention provides a novel a (dichlorotetramethyl)disilazane compound that can enhance the adhesive strength between a photoresist film and a substrate, or between the photoresist and its underlying structures.

The (dichlorotetramethyl)disilazane compound is represented in accordance with the following chemical formula (I),

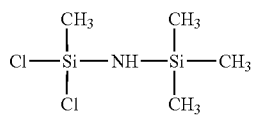

For example, hexamethyldisilazane (HMDS) reacts with trichloromethylsilazane according to the following reaction equation (I) to synthesize the (dichlorotetramethyl)disilazane compound.

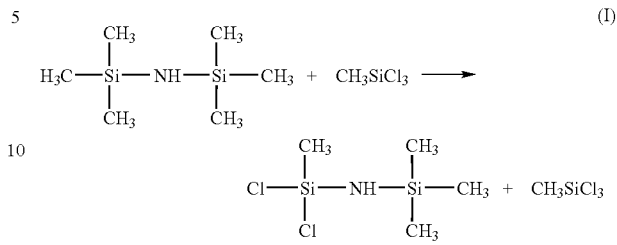

EXAMPLE

Synthesis of (dichlorotetramethyl)disilazane Compound

A magnetic stir bar was placed into a cooled flask under nitrogen atmosphere. Then in room temperature, hexamethyldisilazane of chemical formula (I) and trichloromethylsilazane of chemical formula (II) were poured into the flask. The weight ratio of hexamethyldisilazane relative to trichloromethylsilazane was about 3:1.

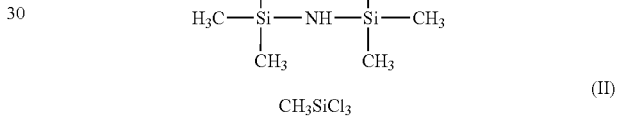

When the attained compound was analyzed using a proton magnetic resonance (1H-NMR) spectroscopy with $C_6D_6$ as a solvent, a chemical shift (δ-shift) of about 0.03 ppm (s, 9H) and a chemical shift of about 0.47 ppm (s, 3H) were obtained. Thus, the attained compound was identified as a novel silazane compound.

The (dichlorotetramethyl)disilazane can be used as an adhesive agent for a photoresist film having strong hydrophobic characteristics, which are exposed with an argon fluoride (ArF) laser. A viscosity of the (dichlorotetramethyl)disilazane compound is less than or substantially similar to that of water. Thus, the photoresist film is not lifted from its underlying structure, if the (dichlorotetramethyl)disilazane compound is interposed therebetween. Additionally, when the photoresist film is baked after the photoresist film is formed on the substrate, the (dichlorotetramethyl)disilazane compounds cross-link with each other to thereby enhance the adhesive strength between the photoresist film and the substrate, or between the photoresist film and its underlying structure.

FIG. 1 is a flow chart illustrating a method of enhancing the adhesive strength between a photoresist film and a substrate, or between a photoresist film and its underlying structure in accordance with one embodiment of the present invention.

In step S110, an adhesive layer having an adhesive compound in accordance with the above chemical formula (I) is formed on a substrate. Then, in step S120 a photoresist film is formed on the adhesive layer. In step S130, the substrate and the photoresist film are baked to enhance the adhesive strength between the photoresist film and the substrate.

In further detail, in step S110, the adhesive layer is formed on the substrate having an underlying structure thereunder. For example, the substrate is silicon, and the underlying structure is a conductive layer for a bit line or a gate electrode, or an insulating layer such as a nitride layer for a spacer. The spacer is preferably used to form a self-aligned contact.

In step S120, the photoresist film is formed on the adhesive layer. The photoresist film is either a positive photoresist composition or a negative photoresist composition. The photoresist film is preferably formed on the substrate by a spin coating process. Alternatively, an anti-reflective layer (ARL) may be formed between the substrate and the photoresist film to ensure a process margin.

In step S130, the substrate, the photoresist film, and the adhesive layer are baked. For example, the baking temperature is preferably at a temperature of about 90° C. to about 120° C. When the temperature of the baking process is substantially lower than about 90° C., solvents in the photoresist film may not be completely removed from the photoresist film. If the remaining solvents are exposed to light, a chemical reaction may occur, and the photoresist film may not properly develop. Further, the solvents may interrupt the cross-linking of the adhesive compounds and reduce the adhesive strength between the photoresist film and the substrate. As a result, a photoresist pattern formed on the substrate may easily collapse.

If the temperature of the baking process is substantially greater than about 120° C., portions of the positive photoresist compound sensitive to light might get damaged. Additionally, if the photoresist composition is negative, portions of the photoresist composition not exposed to light may be polymerized by heat, which generates residue on the photoresist pattern.

In the baking process, the adhesive compounds cross-link with each other to form a polymer in accordance with reaction equations (II) and (III):

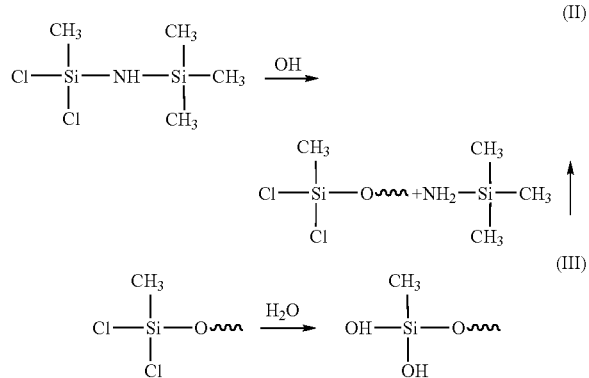

The present invention also provides a method for forming a photoresist pattern using a (dichlorotetramethyl)disilazane compound.

Figure 2:
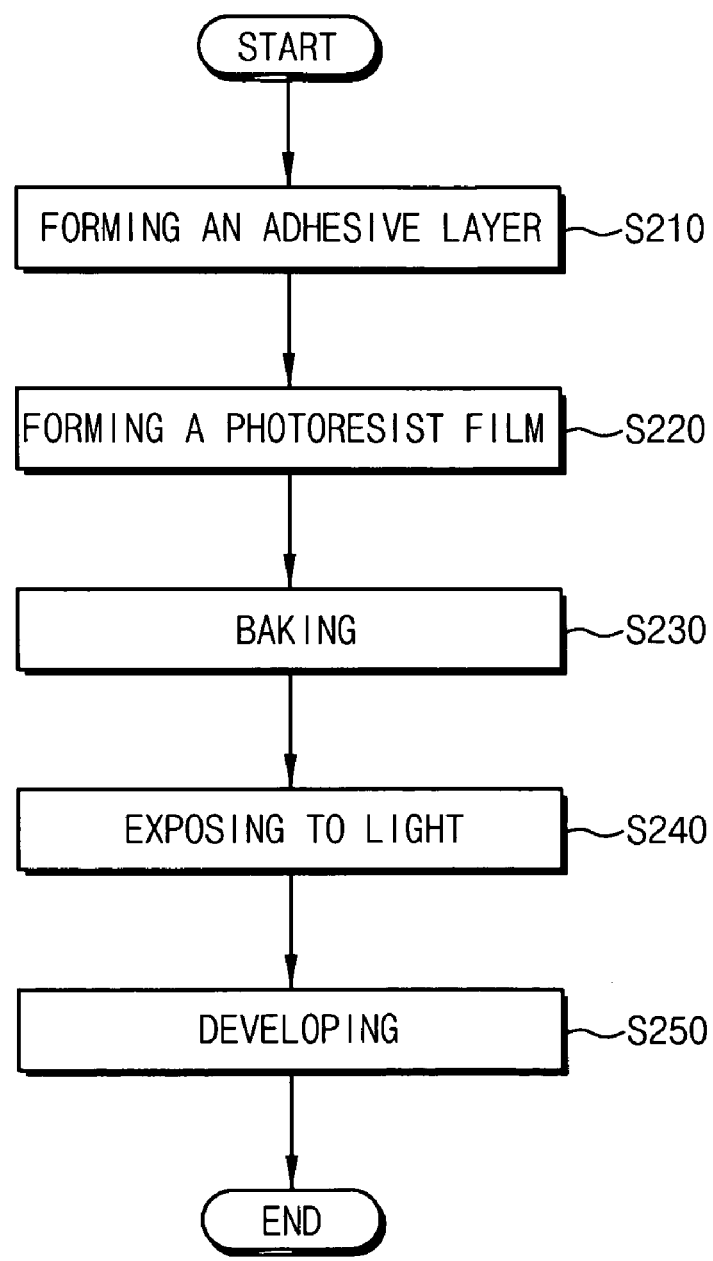
FIG. 2 is a flow chart illustrating a method of forming a photoresist pattern in accordance with one embodiment of the present invention.

FIG. 2 is a flow chart illustrating a method for forming a photoresist pattern in accordance with one embodiment of the present invention.

After an adhesive layer having the compound in accordance with the above chemical formula (I) is formed in step S210, in step S220, a photoresist film is formed on the adhesive layer. In step S230, the substrate and the photoresist film are baked to enhance an adhesive strength between each other. Steps S210 to S230 are substantially identical to steps S110 to S130 to enhance the adhesive strength between the substrate and the photoresist film. In step S240, the baked photoresist film is exposed to light. And finally in step S250, the photoresist film is developed to form a photoresist pattern.

FIGS. 3A to 3E are cross-sectional views illustrating a method of forming a photoresist pattern in accordance with one embodiment of the present invention.

Figure 3A:
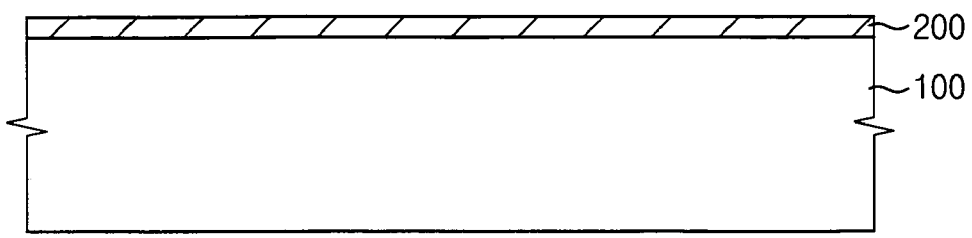
FIGS. 3A to 3E are cross-sectional views illustrating a method of forming a photoresist pattern in accordance with one embodiment of the present invention.

Referring to FIG. 3A, an adhesive layer 200 in accordance with the above chemical formula is formed on a substrate 100.

Figure 3B:
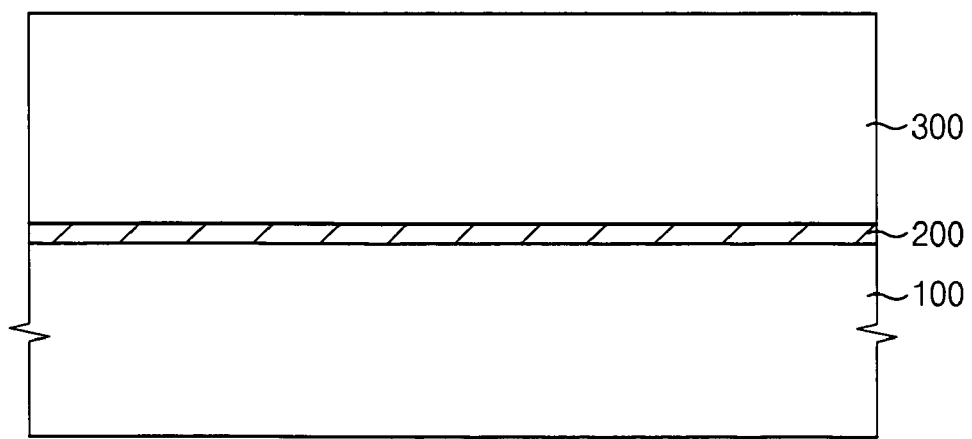

Referring to FIG. 3B, a photoresist film 300 is formed on adhesive layer 200. Photoresist film 300 is a positive photoresist composition or a negative photoresist composition. Photoresist film 300 is preferably formed on adhesive layer 200 by a spin-coating process. In addition, an anti-reflective layer (ARL) is optionally formed between substrate 100 and photoresist film 300 to ensure a process margin.

Figure 3C:
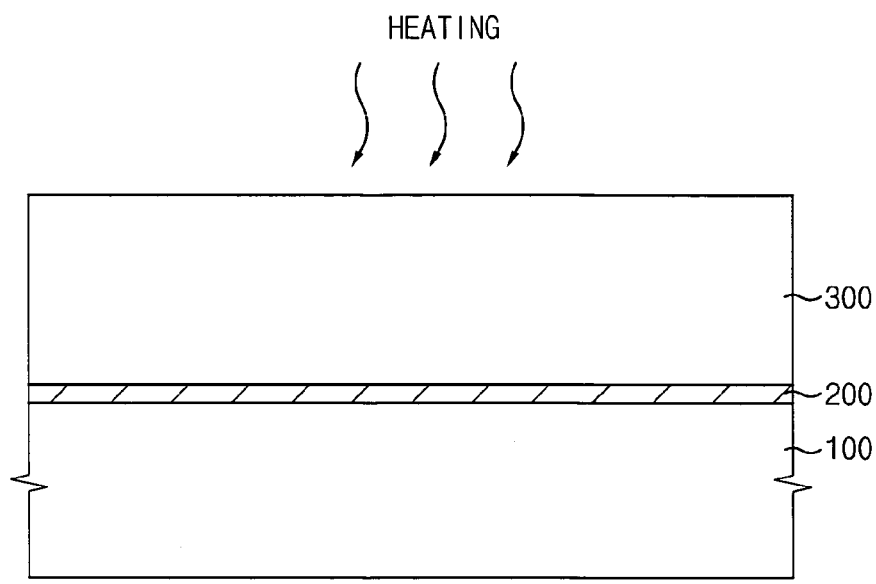

Referring to FIG. 3C, substrate 100 and photoresist film 300 are baked. The baking temperature is preferably about 90° C. to about 120° C. The (dichlorotetramethyl)disilazane compounds cross-link with each other (above reaction equations (II) and (III)) to form a polymer that tightly attaches photoresist film 300 to substrate 100.

Figure 3D:
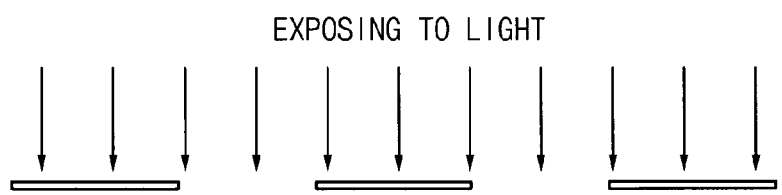
Figure 3D:
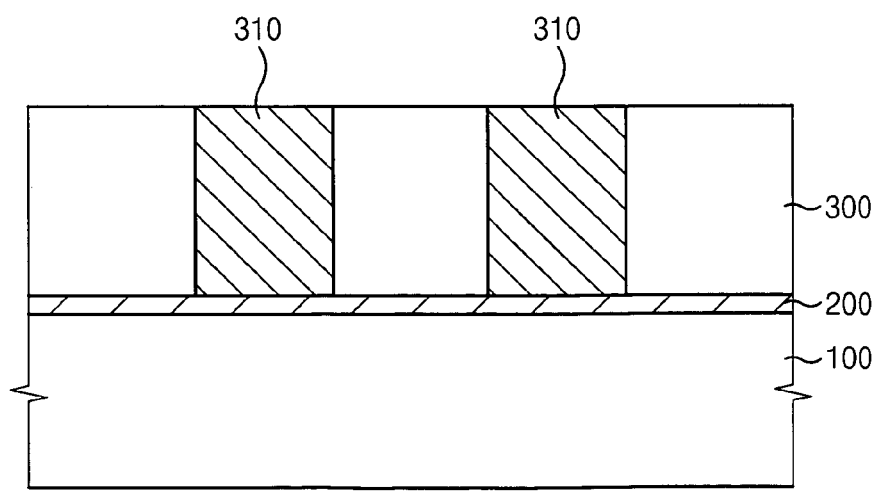

Referring to FIG. 3D, using a mask, photoresist film 300 is exposed to light. In detail, a mask having a pattern is positioned over photoresist film 300. Here, the mask selectively exposes predetermined portions 310 of the photoresist film 300. Then, photoresist film 300 is exposed to the light passing through the mask. For example, the light may be a G-line, an I-line, a krypton fluoride (KrF) laser, an argon fluoride (ArF), an e-beam laser, an X-ray, etc. Preferably, a light having a wavelength (λ) less than or substantially identical to a wavelength of ArF laser (λ is about 193 nm) is employed to manufacture a semiconductor device having a pattern having a line width of several tens of nanometers. Thus, exposed portions 310 have different solubility from that of unexposed portions of photoresist film 300.

Figure 3E:
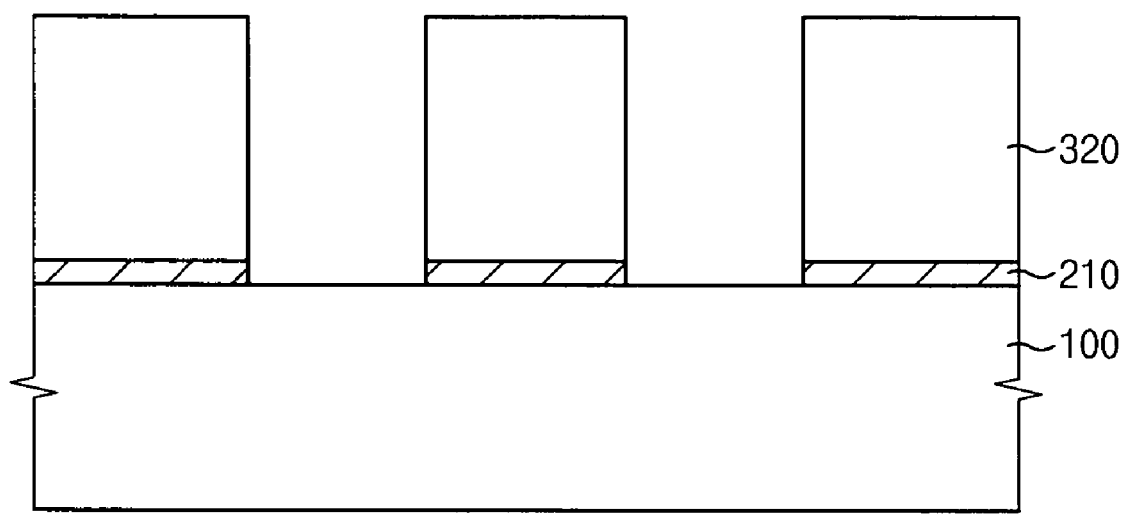

Referring to FIG. 3E, exposed portion 310 of photoresist film 300 is developed to form a photoresist pattern 320. For example, when photoresist film 300 is a positive photoresist composition, exposed portions 310 of are removed using a developing solvent such as tetramethylammoniumhydroxide (TMAH). When photoresist pattern 320 is formed on substrate 100, an adhesive layer pattern 210 is interposed between substrate 100 and photoresist pattern 320.

A hardening process and a cleaning process are subsequently performed to complete the formation of photoresist pattern 320. An underlying structure such as a metal line or an insulating layer pattern is preferably formed on substrate 100 using photoresist pattern 320 as a mask.

The silazane compound of the present invention enhances the adhesive strength between the photoresist film and the underlying structure formed on the substrate or between the photoresist film and the substrate. In addition, the silazane compound of the present invention effectively prevents the photoresist pattern formed on the substrate from collapsing. Thus, fine patterns on the semiconductor device are accurately formed using the silazane compound.

Accordingly, a semiconductor device having improved reliability is economically manufactured when an adhesive layer having the silazane compound of the present invention is provided between a photoresist film and a substrate. Additionally, manufacturing cost and time required for manufacturing the semiconductor device is reduced.

What is claimed is:

1. A (dichlorotetramethyl)disilazane compound having the chemical formula,

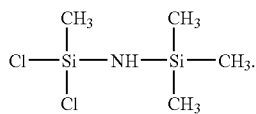

2. The method of claim 1, wherein the adhesive compound exhibits a chemical shift (δ-shift) of about 0.03 ppm (s, 9H) and a chemical shift of about 0.47 ppm (s, 3H) when the adhesive compound is analyzed with proton magnetic resonance (1H-NMR) spectroscopy using $C_6D_6$ as a solvent.

3. The compound of claim 1, wherein baking is performed at a temperature of about 90° C. to about 120° C.

4. The method of claim 1, further comprising forming an anti-reflective layer between the substrate and the adhesive layer.

5. The method of claim 1, further comprising forming a conductive layer or an insulating layer between the substrate and the adhesive layer.

6. The method of claim 1, further comprising exposing the photoresist film to a light; and
developing the photoresist film to form a photoresist pattern on the substrate.

7. The method of claim 5, wherein the light is a G-line, an I-line, a krypton fluoride laser, an argon fluoride laser, an e-beam, or an X-ray.

8. A method for forming a photoresist pattern comprising:
forming an adhesive layer containing an adhesive compound having the following chemical formula on a substrate,

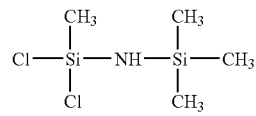

forming a photoresist film on the adhesive layer;
baking the photoresist film formed on the substrate;
exposing the photoresist film to a light; and
developing the photoresist film to form a photoresist pattern on the substrate.

9. The method of claim 8, wherein the adhesive compound exhibits a chemical shift (δ-shift) of about 0.03 ppm (s, 9H) and a chemical shift of about 0.47 ppm (s, 3H) when the compound is analyzed with proton magnetic resonance (1H-NMR) spectroscopy using $C_6D_6$ as a solvent.

10. The method of claim 8, wherein the light is a G-line, an I-line, a krypton fluoride laser, an argon fluoride laser, an e-beam, or an X-ray.

11. The method of claim 8, wherein baking is performed at a temperature of about 90° C. to about 120° C.

12. The method of claim 8, further comprising forming a conductive layer or an insulating layer between the substrate and the adhesive layer.

13. The method of claim 8, wherein the adhesive compound is cross-linked another adhesive compound in accordance with baking the photoresist film.

* * * * *